(12) United States Patent
Bally et al.

(10) Patent No.: US 7,314,200 B2
(45) Date of Patent: Jan. 1, 2008

(54) SUPPORT AND TRANSPORT SYSTEM FOR MEDICAL APPARATUS

(75) Inventors: Alex Bally, Barrington, RI (US); Wendell Wilson, Marietta, GA (US); George Gounaris, West Palm Beach, FL (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 10/844,908

(22) Filed: May 13, 2004

(65) Prior Publication Data

US 2005/0253034 A1    Nov. 17, 2005

(51) Int. Cl.
*E04G 3/00* (2006.01)

(52) U.S. Cl. .............................. 248/276.1; 248/282.1; 248/283.1; 248/289.11; 248/122.1; 248/124.1

(58) Field of Classification Search ............. 248/276.1, 248/282.1, 283.1, 289.11, 122.1, 124.1
See application file for complete search history.

(56) References Cited

U.S. PATENT DOCUMENTS

| | | | | |
|---|---|---|---|---|
| 1,938,643 A | * | 12/1933 | Smith ...................... | 248/276.1 |
| 2,470,524 A | * | 5/1949 | Scudder ................... | 248/122.1 |
| 2,696,963 A | * | 12/1954 | Shepherd ................. | 248/229.15 |
| 3,835,486 A | * | 9/1974 | Benoit et al. ............. | 5/503.1 |
| 4,489,454 A | * | 12/1984 | Thompson ............... | 5/503.1 |
| 4,557,453 A | * | 12/1985 | McCloskey .............. | 248/287.1 |
| 4,700,922 A | * | 10/1987 | Gross ...................... | 248/558 |
| 4,714,222 A | * | 12/1987 | Kiesel et al. ............. | 248/282.1 |
| 4,725,027 A | * | 2/1988 | Bekanich ................. | 248/125.8 |
| 4,795,122 A | | 1/1989 | Petre ....................... | 248/317 |
| 4,832,299 A | | 5/1989 | Gorton et al. ............ | 248/231.7 |
| 4,886,237 A | * | 12/1989 | Dennis .................... | 248/289.11 |
| 4,893,810 A | | 1/1990 | Lee ......................... | 272/123 |
| 4,945,592 A | * | 8/1990 | Sims et al. ............... | 5/658 |
| 5,118,127 A | * | 6/1992 | Partington ............... | 280/488 |
| 5,135,191 A | * | 8/1992 | Schmuhl .................. | 248/125.1 |
| 5,219,139 A | * | 6/1993 | Hertzler et al. .......... | 248/276.1 |
| 5,236,162 A | * | 8/1993 | Desjardins ............... | 248/214 |
| 5,236,213 A | * | 8/1993 | Trickett ................... | 280/304.1 |
| 5,319,816 A | * | 6/1994 | Ruehl ...................... | 5/600 |
| 5,344,169 A | * | 9/1994 | Pryor et al. .............. | 280/79.3 |
| 5,355,539 A | * | 10/1994 | Boettger .................. | 5/503.1 |
| 5,379,205 A | * | 1/1995 | Peng ....................... | 362/430 |
| 5,385,324 A | * | 1/1995 | Pryor et al. .............. | 248/228.3 |
| 5,421,548 A | * | 6/1995 | Bennett et al. ........... | 248/129 |
| 5,509,680 A | * | 4/1996 | Scharf et al. ............. | 280/304.1 |
| 5,556,065 A | * | 9/1996 | Wadley .................... | 248/129 |
| 5,588,166 A | * | 12/1996 | Burnett .................... | 5/503.1 |
| 5,597,146 A | * | 1/1997 | Putman .................... | 248/276.1 |
| 5,987,670 A | | 11/1999 | Sims et al. ............... | 5/600 |

(Continued)

*Primary Examiner*—Carl D. Friedman
*Assistant Examiner*—Michael McDuffie
(74) *Attorney, Agent, or Firm*—Kusner & Jaffe; Michael A. Centanni (57) ABSTRACT

A support and transport system for a patient care apparatus comprised of a first arm assembly connected to a stationary support and a second arm assembly connected to a patient transfer vehicle. An end cap for supporting a patient care apparatus is selectively attachable to the first arm assembly and to the second arm assembly. Locking means are provided on the end cap for locking the end cap onto one of the first and second arm assemblies. The other of the first and second arm assemblies is detachable from the end cap only when the end cap is locked onto the one of the first and second arm assemblies.

64 Claims, 10 Drawing Sheets

U.S. PATENT DOCUMENTS

| | | | |
|---|---|---|---|
| 6,179,260 B1 * | 1/2001 | Ohanian | 248/229.16 |
| 6,182,662 B1 * | 2/2001 | McGhee | 128/845 |
| 6,382,576 B1 | 5/2002 | Heimbrock | 248/227.3 |
| 6,585,206 B2 * | 7/2003 | Metz et al. | 248/229.1 |
| 6,704,956 B2 * | 3/2004 | Riley et al. | 5/600 |

* cited by examiner

SUPPORT AND TRANSPORT SYSTEM FOR MEDICAL APPARATUS

FIELD OF THE INVENTION

The present invention relates generally to transport systems, and more specifically, to a system for supporting and transporting one or more medical apparatus used in the care of a patient.

BACKGROUND OF THE INVENTION

In modern hospitals and medical facilities, a great deal of medical equipment is used in the care and treatment of patients. In this respect, it is quite common for a patient to be connected to a number of different medical apparatus, such as pumps administrating intravenous (IV) fluids, monitors, oxygen tanks, electrical strips and the like. Typically, these medical apparatus are mounted onto a vertical pole, conventionally referred to as an "IV pole." It has been known to support IV poles on a wheeled basis that can be positioned adjacent a hospital bed or can be transported with the bed to another location.

In recent years, the size and number of medical apparatus routinely attached to a patient has increased, thus requiring more sturdy IV pole structures for supporting such equipment. For these and other reasons, it is necessary that an IV pole and its associated medical apparatus be firmly supported near a patient. In this respect, mounting the IV pole and its associated apparatus to a rigid wall or column is becoming preferable because it provides better structural support for the IV pole.

At the same time, it is often necessary to transport the patient, together with the medical apparatus that is operatively connected to the patient, to another location in the hospital for medical procedures or testing. At these times, it is necessary that the IV poles and medical apparatus be easily transferred from the wall or column support to a hospital bed, or to some other patient transfer vehicle, for movement to another location.

The present invention provides a support and transport system for supporting and transporting one or more medical apparatus between a wall support and a patient transfer vehicle, which system provides positive transfer from one to another, and vice-a-versa.

SUMMARY OF THE INVENTION

In accordance with the present invention, there is provided a support and transport system for a patient care apparatus, comprised of a first arm assembly connected to a stationary support and a second arm assembly connected to a patient transfer vehicle. An end cap for supporting a patient care apparatus is selectively attachable to the first arm assembly and to the second arm assembly. Locking means are provided on the end cap for locking the end cap onto one of the first and second arm assemblies. The other of the first and second arm assemblies is detachable from the end cap only when the end cap is locked onto the one of the first and second arm assemblies.

In accordance with another aspect of the present invention, there is provided in combination, an IV pole, a first arm assembly connectable to a first structure, a second arm assembly connectable to a second structure, and an end cap for supporting the patient care apparatus. The end cap is selectively attachable to the first arm assembly and to the second arm assembly. Locking means are provided on the end cap for locking the end cap onto one of the first and second arm assemblies. The other of the first and second arm assemblies is detachable from the end cap only when the end cap is locked onto the one of the first and second arm assemblies.

In accordance with another aspect of the present invention, there is provided a support and transport system for a patient care apparatus comprised of a first arm assembly connected to a first structure and a second arm assembly connected to a second structure. An end cap for supporting a patient care apparatus is selectively attachable to the first arm assembly and to the second arm assembly. Locking means are provided on the end cap for locking the end cap onto one of the first and second arm assemblies. The other of the first and second arm assemblies is detachable from the end cap only when the end cap is locked onto the one of the first and second arm assemblies.

An advantage of the present invention is a support and transport system that allows transfer of patient care apparatus between a stationary support and a patient transport vehicle.

Another advantage of the present invention is a support and transport system that allows transfer of one or more IV poles, having one or more medical apparatus thereon, between a stationary support and a patient transfer vehicle.

Another advantage of the present invention is a support and transport system that insures positive transfer of an IV pole and the attendant apparatus from a stationary support to a patient transfer vehicle and vice-a-versa, or between two patient transfer vehicles.

A still further advantage of the present invention is a support and transport system that physically locks an IV pole to either a stationary support or a patient transfer vehicle.

A still further advantage of the present invention is a support and transport system that provides an indication that an IV pole, and its attendant apparatus, is locked to either the patient transfer vehicle or to a wall support.

Another advantage of the present invention is a support and transport system wherein a patient and IV equipment operatively attached to the patient can be quickly transferred from one location within a hospital to another.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
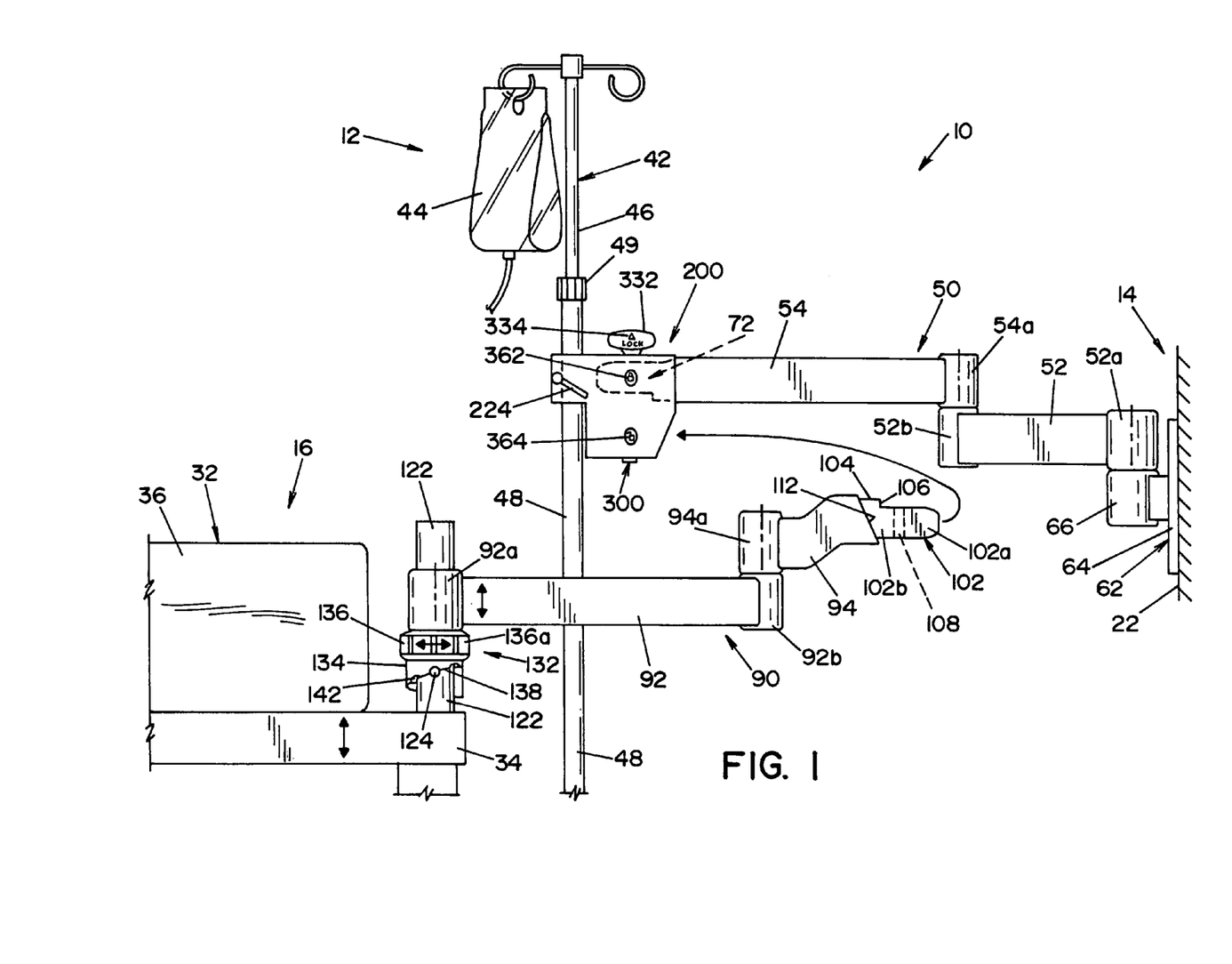
FIG. 1 is an elevational view showing a support and transport system for an IV pole, illustrating a preferred embodiment of the present invention.

Referring now to the drawings wherein the showings are for the purpose of illustrating preferred embodiments of the invention only, and not for the purpose of limiting same, FIG. 1 is an elevational view showing a support and transport system 10 for transferring patient care apparatus 12 between a stationary support 14 and a patient transfer vehicle 16, illustrating a preferred embodiment of the present invention. As used herein, the term "stationary support" refers to any permanent, rigid structure, such as by way of example and not limitation, a wall, support, a patient headwall or a structural support column. The term "patient transfer vehicle" refers to any type of medical structure used to support and transfer patients from one location to another, such as by way of example and not limitation, a hospital bed, a hospital stretcher, a surgical chair or a wheel chair. In the embodiment shown, stationary support 14 is comprised of a wall 22, and patient transfer vehicle 16 is comprised of a hospital bed 32 having a frame 34 and a mattress 36 thereon. In the embodiment shown, patient care apparatus 12 is comprised of an IV pole 42 supporting a conventional intravenous (IV) solution bag 44. However, as will be appreciated from a further reading of the specification, system 10 may find advantageous application in supporting and transferring other types of patient care apparatus 12.

In the embodiment shown, support and transport system 10 is comprised of a first arm assembly 50 attached to wall 22, a second arm assembly 90 attached to hospital bed 32 and an end cap 200 for supporting patient care apparatus 12, end cap 200 being connectable to either of first or second arm assemblies 50, 90.

In the embodiment shown, first arm assembly 50 is comprised of a proximal arm 52 and a distal arm 54. First arm assembly 50 is mounted to a wall bracket 62 that is attached to wall 22. Wall bracket 62 is comprised of a plate 64 having a support or mount 66 attached thereto. Plate 64 is adapted to be fixedly secured to wall 22 by conventional fasteners (not shown). In the embodiment shown, mount 66 is shaped in the form of a hub. Proximal arm 52 is an elongated member having cylindrical hubs 52a, 52b formed at both ends. A bored opening (not shown) is formed in hub 52a to receive a pin so as to pivotally connect one end of proximal arm 52 to wall bracket. In this respect, the proximal arm 52 is pivotally moveable in a horizontal plane about the axis of the pin that connects the end of proximal arm 52 to bracket 62. Distal arm 54 is an elongated member having a hub 54a formed at one end. A bored opening is formed in hub 54a to receive a pin to pivotally mount distal arm 54 to proximal arm 52 to allow movement of distal arm 54 relative to proximal arm 52 about the axis of the pin connecting distal arm 54 to proximal arm 52.

Figure 2:
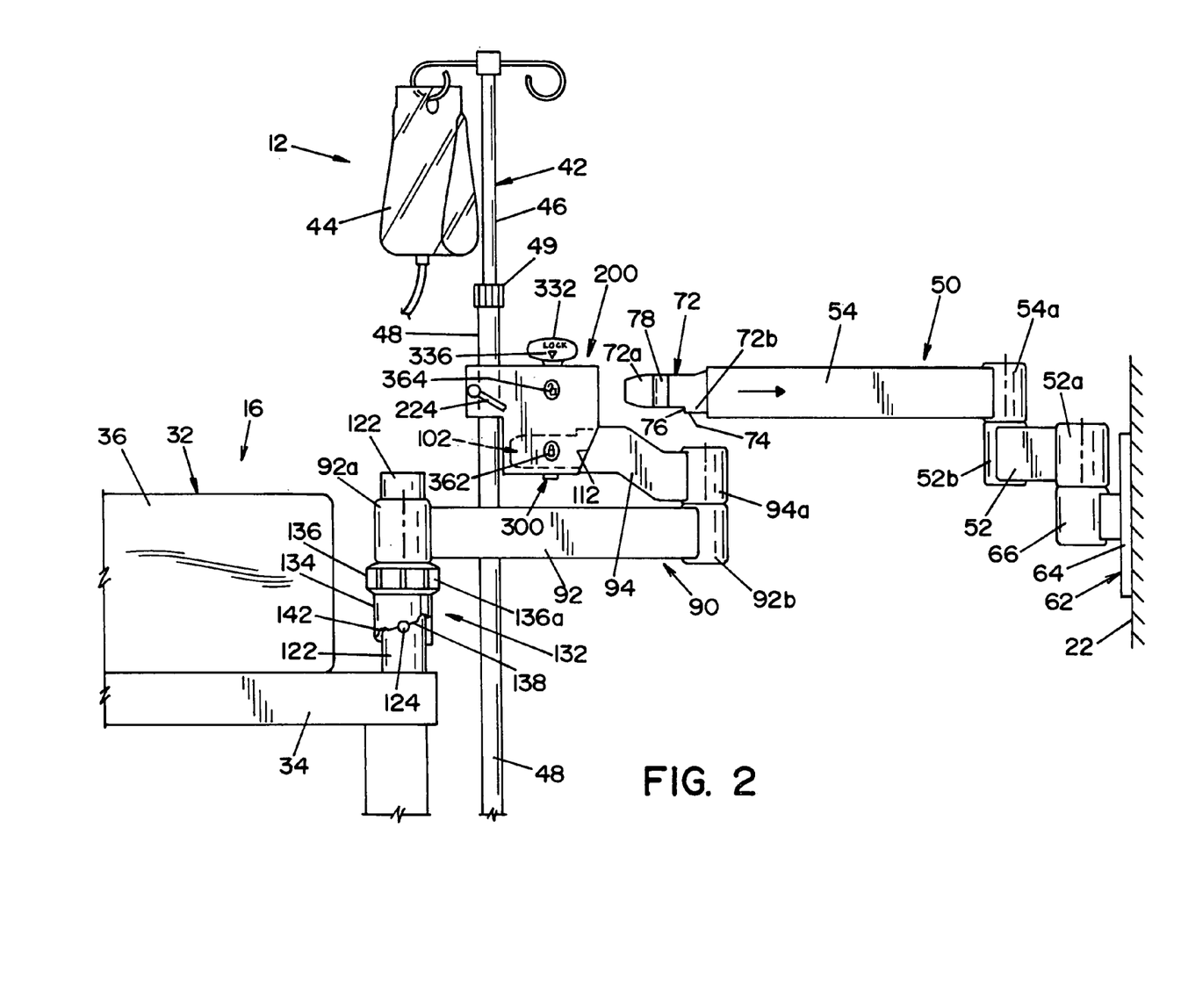
FIG. 2 is an elevational view of the support and transport system shown in FIG. 1, showing such system immediately after an IV pole has been transferred from a wall support to a patient transfer vehicle.
Figure 4:
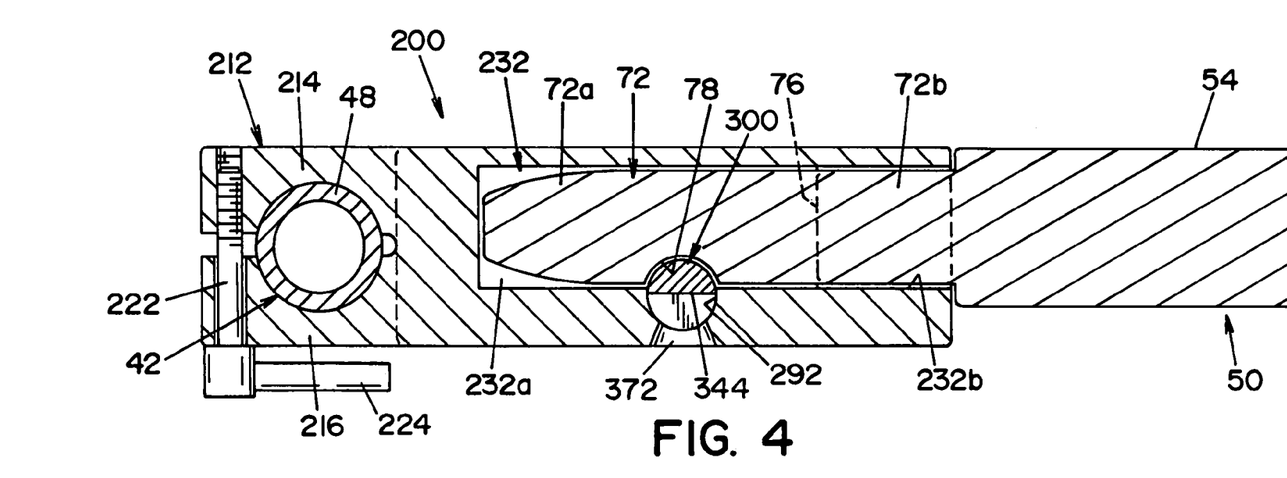
FIG. 4 is a sectional view taken along lines 4-4 of FIG. 3.

The free end of distal arm 54 is formed to have a plate-like extension 72, best seen in FIG. 2. The extension has a tongue-shaped portion 72a and a rectangular side portion 72b. A shoulder 74 having an abutment surface 76 is defined between tongue-shaped portion 72a and side portion 72b of the extension. A groove 78 is formed in one side face of extension 72. Groove 78 is generally semi-circular in shape, as best seen in FIG. 4.

As indicated above, second arm assembly 90 is dimensioned to be attached to patient transfer vehicle 16, that in the embodiment shown is hospital bed 32. Second arm assembly 90 includes proximal arm 92 and distal arm 94. Proximal arm 92 is an elongated member having cylindrical hubs 92a, 92b formed at the ends thereof. Hub 92a has a bored opening dimensioned to allow the one end of proximal arm 92 to be pivotally mounted onto a vertical post 122 on bed frame 34, as illustrated in FIG. 2, as will be described in greater detail below. Distal arm 94 is an elongated, serpentine-shaped member having a hub 94a formed at one end. A bored opening is formed through hubs 92b, 94a to allow proximal arm 92 to be pinned to distal arm 94. In this respect, distal arm 94 and proximal arm 92 are pinned together to allow rotation of distal arm 94 relative to proximal arm 92 in a horizontal plane about the axis of the pin connecting distal arm 94 to proximal arm 92. The free end of distal arm 94 is formed to include a generally rectangular, plate-like extension 102, best seen in FIG. 3. Extension 102 has a tongue-shaped portion 102a and a rectangular side portion 102b. As shown in the drawings, the free end of tongue-shaped portion 102a is tapered in all directions over a portion of the length thereof. A shoulder 104 having an abutment surface 106 is defined between tongue-shaped portion 102a and side portion 102b of extension 102. As with extension 72 of first arm assembly 50, a semi-cylindrically shaped groove 108 is formed across one face of extension 102. Groove 108 in extension 102 is dimensioned to have the same shape as groove 78 in extension 72 of first arm assembly 50. In the embodiment shown, a tapered surface 112 is defined where extension 102 is joined to the end of distal arm 94. First and second arm assemblies 50, 90 are preferably formed of a metal material to provide sufficient structural strength.

In the embodiment shown, second arm assembly 90 is mounted to bed 32 on a vertically oriented, cylindrical post 122 for pivotal rotation about the axis of post 122. Adjustment means 132 for vertically adjusting the position of second arm assembly 90 on post 122 is provided. Adjustment means 132 is comprised of a sleeve 134 having collar 136 at the upper end thereof. Sleeve 134 and collar 136 are dimensioned to be mounted on post 122 and to be moveable along the outer cylindrical surfaces thereof. The lower end of sleeve 134 is formed to define a ramped, or sloped surface 138 having a plurality of spaced-apart sockets 142 formed therein. Sockets 142 are dimensioned to operatively engage a pin 124 on vertical post 122. Rotational movement of sleeve 134 causes the upper surface of collar 136 to move vertically depending upon the position of helical surface 138 relative to support pin 124. By gripping surface 136a of collar 136 and rotating the same, sleeve 134 may be rotated to allow pin 124 to rest in any of sockets 142, thereby raising and lowering the upper surface of collar 136, and second arm assembly 90.

Figure 3:
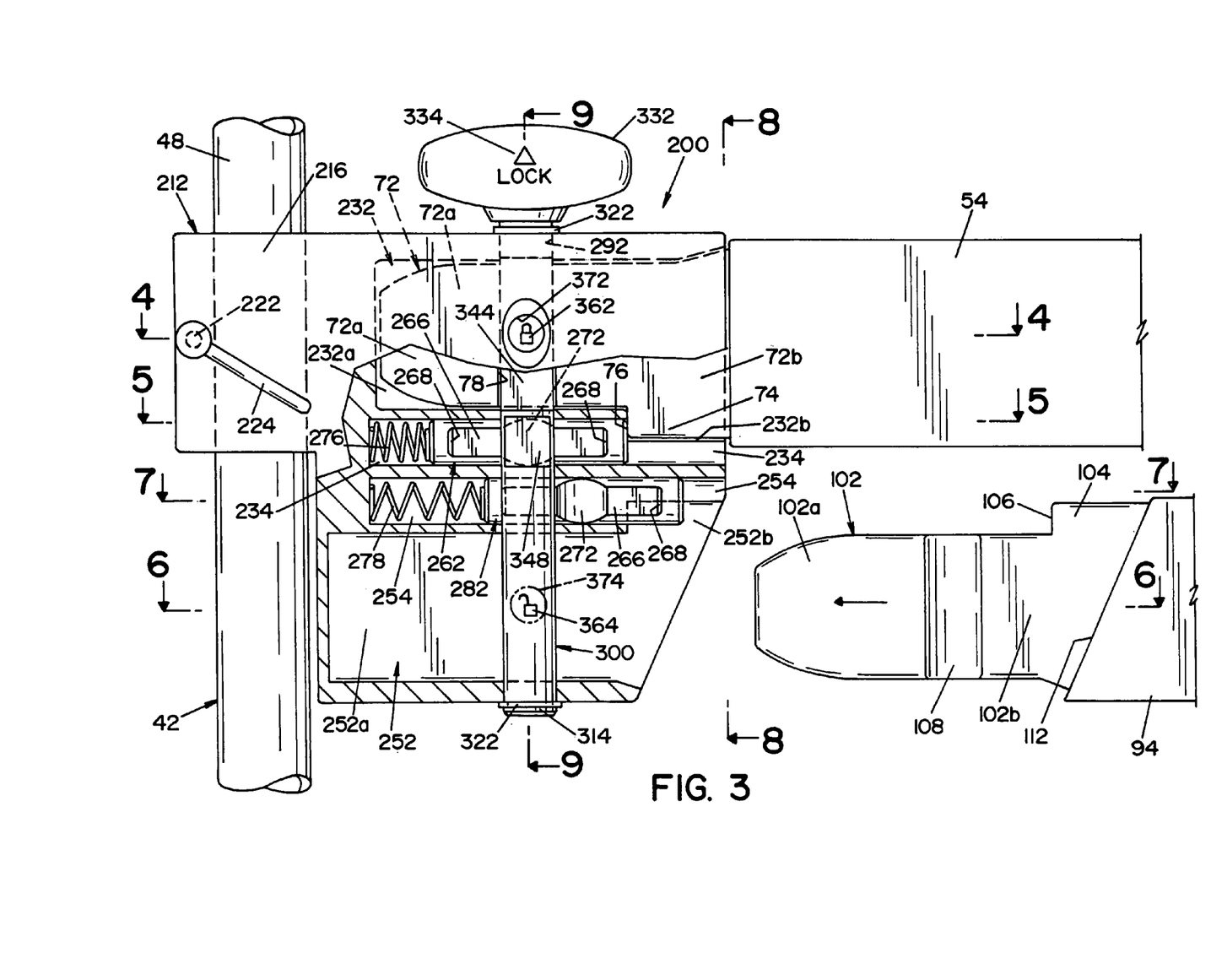
FIG. 3 is an enlarged, elevational view of an end cap for attaching an IV pole to either a wall support or a patient transfer vehicle.

Referring now to FIG. 3, end cap 200 is best seen. End cap 200 is provided to attach to, or be part of, patient care apparatus 12. In the embodiment shown, IV pole 42 is shown attached to end cap 200. IV pole 42 is shown supporting a conventional intravenous solution bag 44, but could also include by way of example and not limitation, monitors, IV pumps, bags containing intravenous solutions and other medical apparatus. In the embodiment shown, IV pole 42 has an upper section 46 and a lower tubular section 48. Upper section 46 is slidably received in lower section 48 and extends therefrom. In this respect, the position of upper section 46 relative to lower section 48 is adjustable by means of a locking ring or collar 49, as is conventionally known.

Figure 5:
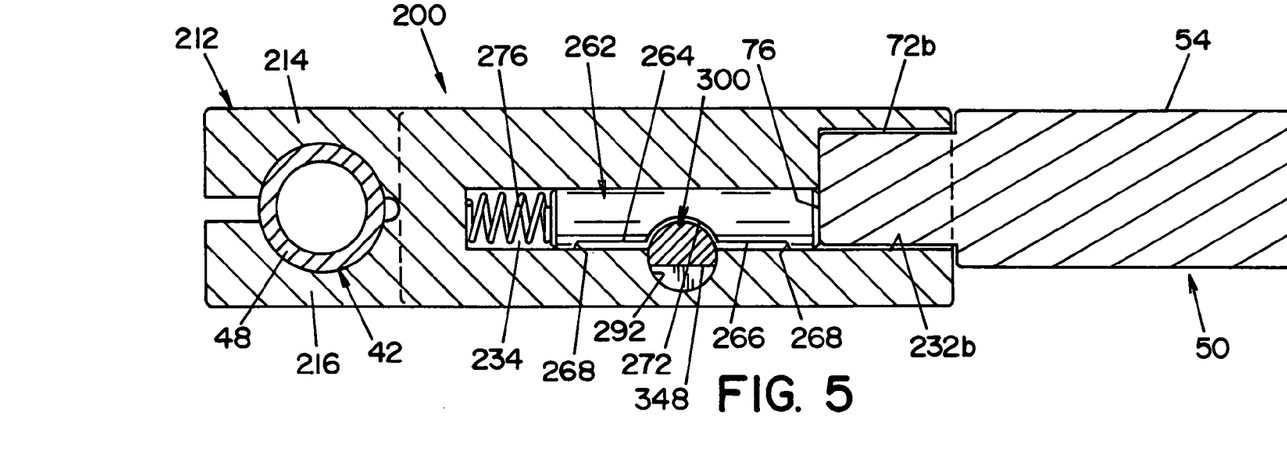
FIG. 5 is a sectional view taken along lines 5-5 of FIG. 3.

End cap 200 includes attachment means for attaching one or more patient care apparatus or one or more IV poles to end cap 200. In the embodiment shown, end cap 200 is formed to include a collar clamp 212 for capturing and holding lower section 48 of IV pole 42, as best illustrated in FIGS. 4 and 5. It is contemplated that other structural devices may be used to secure a patient care apparatus or an IV pole to end cap 200, without deviating from the present invention. Collar clamp 212 is generally formed of two spaced-apart clamp arms 214, 216 that define a cylindrical opening therebetween. A fastener 222 having a handle or lever 224 extends through an opening in clamp arm 216, and is threadingly received in clamp arm 214. In a manner as conventionally understood, rotation of fastener 222 forces clamp arms 214, 216 together about lower section 48 of IV pole 42, thereby securing same to end cap 200.

An upper cavity 232 and a lower cavity 252 are formed in end cap 200. Upper cavity 232 and lower cavity 252 are dimensioned to receive extensions 72, 102 on first and second arm assemblies 50, 90, respectively. Upper and lower cavities 232, 252 are oriented horizontally to receive extensions 72, 102 when extensions 72, 102 are in a predetermined aligned orientation relative to each other.

Upper cavity 232 has a generally rectangular main chamber 232a dimensioned to receive tongue-shaped portion 72a of extension 72, and a smaller side chamber 232b dimensioned to receive side portion 72b of extension 72. A cylindrical bore 234 is formed in end cap 200 adjacent to upper cavity 232. Bore 234 is positioned to be alongside, but spaced from, main chamber 232a, and to be aligned and in communication with side portion 232b, as best seen in FIGS. 3 and 5. Similarly, lower cavity 252 has a generally rectangular main chamber 252a dimensioned to receive tongue-shaped portion 102a of extension 102, and a smaller side chamber 252b dimensioned to receive side portion 102b of extension 102. A cylindrical bore 254 is formed in end cap 200 adjacent to lower cavity 252. Bore 254 is positioned to be alongside, but spaced from, main chamber 252a, and to be aligned and in communication with side portion 252b, as best seen in FIGS. 3 and 7.

Figure 7:
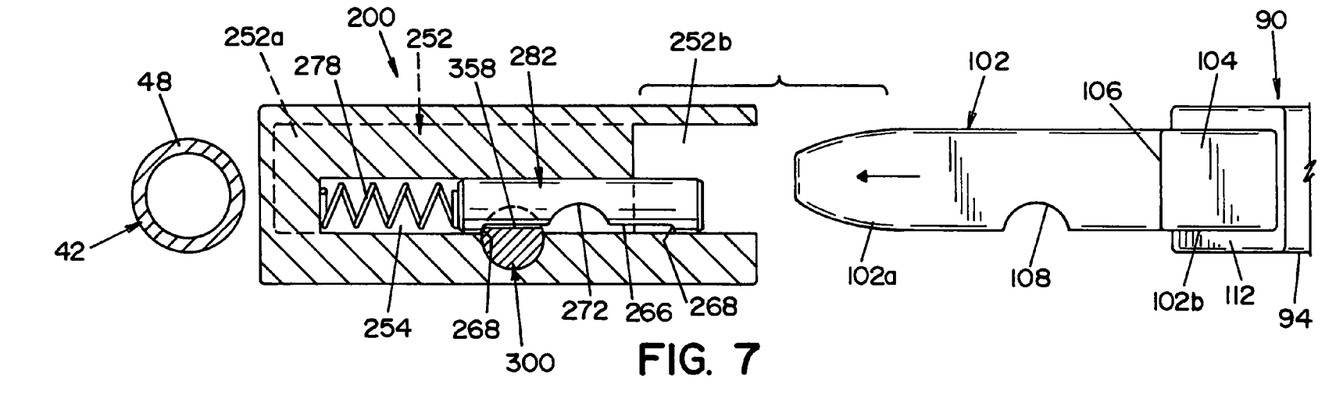
FIG. 7 is a sectional view taken along lines 7-7 of FIG. 3.
Figure 8:
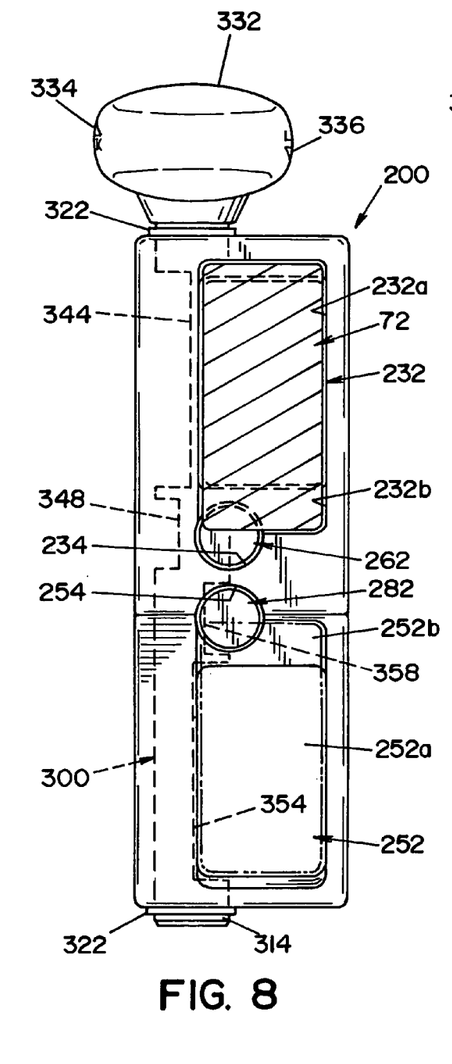
FIG. 8 is a sectional view taken along lines 8-8 of FIG. 3.
Figure 9:
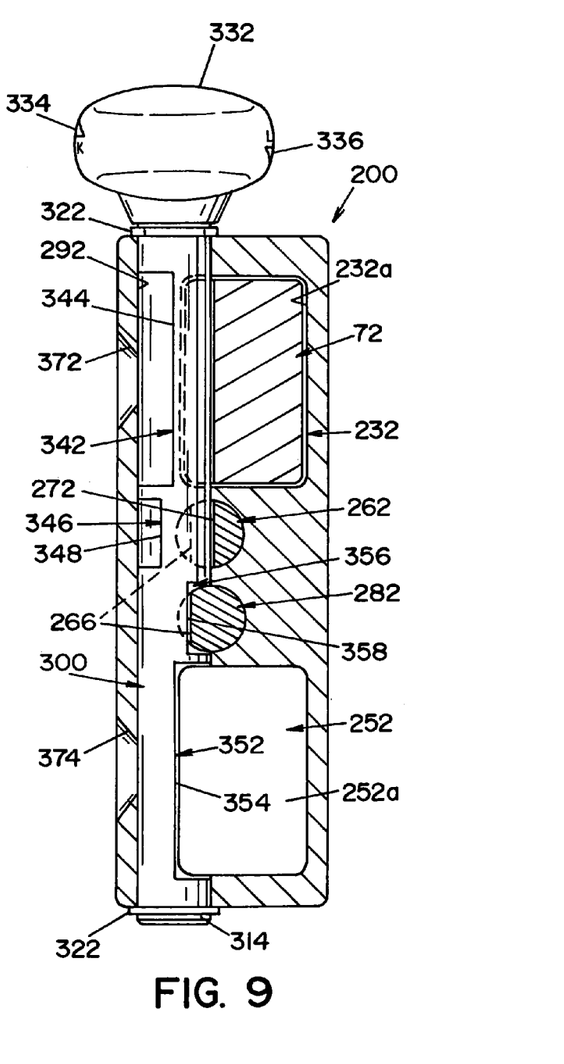
FIG. 9 is a sectional view taken along lines 9-9 of FIG. 3.

As best seen in FIGS. 5 and 7, cylindrical bores 234, 254 formed in upper and lower cavities 232, 252 are disposed to one side of cavities 232, 252. In other words, the central axis of the respective cylindrical bores 234, 254 lie in a generally vertical plane, wherein upper bore 234 is parallel to lower bore 254 and vertically above the lower bore, as shown in FIG. 3. Upper bore 234 is dimensioned to receive a locking pin 262, and lower bore 254 is dimensioned to receive a locking pin 282.

Figure 11:
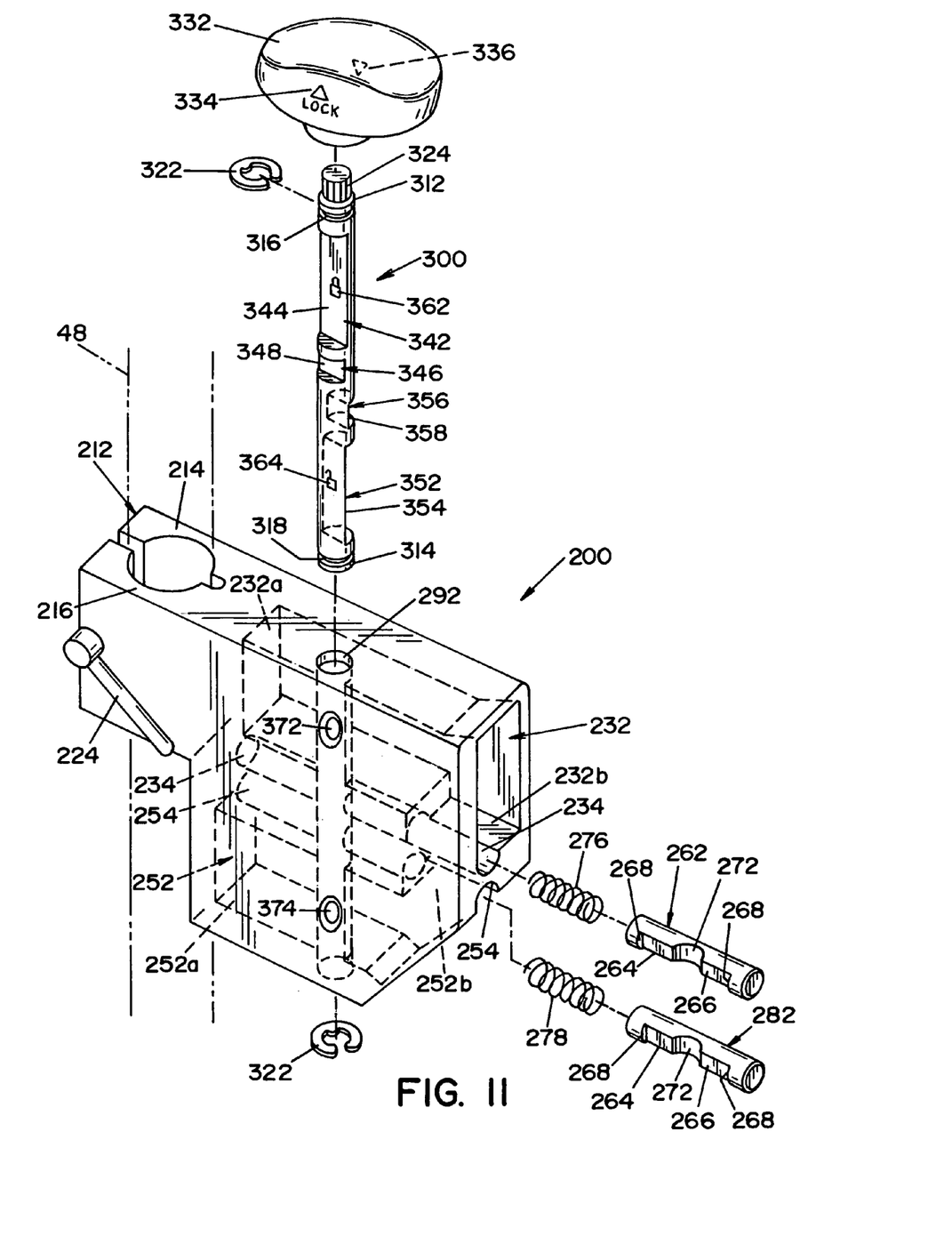
FIG. 11 is an exploded, perspective view of the end cap shown in FIG. 3.

Locking pins 262, 282 are best seen in FIG. 11. Locking pins 262, 282 are generally identical, and therefore, only one shall be described in detail, it being understood that such description applies equally to the other. Locking pin 262 is generally cylindrical in shape, and includes a machined area 264 that defines a flat, planar surface 266 formed along one side of pin 262. Planar surface 266 extends generally parallel to the axis of pin 262. Shoulder surfaces 268 are defined at the ends of flat surface 266 that is defined by machined area 264. A semi-cylindrical notch 272 is formed in flat surface 266 of pin 262. Notch 272 is oriented transverse to the axis of pin 262. Locking pins 262, 282 are dimensioned to be slidably received within cylindrical bores 234, 254 of end cap 200. Biasing elements 276, 278, in the form of helical springs, are disposed between locking pins 262, 282 and the bottom of cylindrical bores 234, 254, as best illustrated in FIGS. 5 and 7. Locking pins 262, 282 are dimensioned to abut surfaces 76, 106 on extensions 72, 102 of first and second arm assemblies 50, 90, as illustrated in FIG. 5, as shall be described in greater detail below.

An elongated cylindrical opening 292 extends through end cap 200, as best seen in FIG. 11. Opening 292 is oriented generally transverse to the axis of cylindrical bores 234, 254 and locking pins 262, 282. Opening 292 is disposed to partially intersect bores 234, 254, as illustrated in FIG. 4-7. Cylindrical opening 292 likewise partially intersects rectangular main chambers 232a, 252a of cavities 232, 252. Cylindrical opening 292 is dimensioned to receive a control rod 300, best illustrated in FIG. 11. Control rod 300 is dimensioned to extend through end cap 200 and to have end portions 312, 314 that project therefrom. Annular grooves 316, 318 are formed at the distal ends of control rod 300 to receive retaining rings 322 to lock control rod 300 in position within cylindrical opening 292. One end of control rod 300 includes a splined portion 324 adapted to receive a knob 332. Knob 332 is generally oval in shape and includes a first knob icon 334 on one side indicating an "upper locked configuration," and a second knob icon 336 on the other side of knob 332 indicating a "lower locked configuration." Control rod 300 is formed to include a first, major cut-out section 342 defining a first major flat 344 and a first minor cut-out section 346 defining a first minor flat 348 formed on one side of the rod. A second major "cut-out" section 352 that defines a second major flat 354 and a second minor cut-out section 356 that defines a second minor flat 358 are formed on the opposite side of rod 300, i.e., 180° offset from said first major and minor cut-out sections 342, 346, as illustrated in FIG. 11. First major and minor cut-out sections 342, 346 and second major and minor cut-out sections 352, 356 are dimensioned and disposed along control rod 300 such that when control rod 300 is disposed within end cap 200, the first major cut-out section 342 and first minor cut-out section 346 are in registry with main rectangular chamber 232a and first cylindrical bore 234, and second major cut-out section 352 and second minor cut-out section 356 are in registry with main rectangular chamber 252a and second cylindrical bore 254, respectively.

Figure 6:
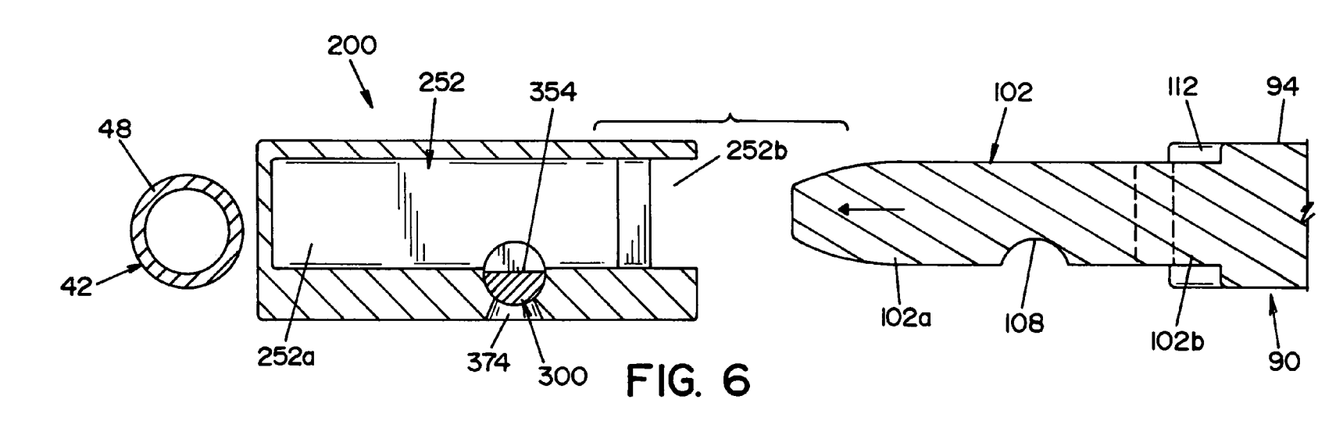
FIG. 6 is a sectional view taken along lines 6-6 of FIG. 3.

In accordance with one aspect of the present invention, icons are provided along the length of control rod 300. A first rod icon 362 indicative of a "locked configuration" is provided on first major flat 344 and second major flat 354. In the embodiment shown, icon 362 is an image of a lock in a closed position. It will of course be appreciated from further reading of the specification that other visual indicia of a locked configuration may be provided without deviating from the present invention. On the opposite sides of control rod 300, i.e., on the rounded, cylindrical surfaces directly opposite to first rod icons 362 on first and second major flats 344, 354, second rod icons 364 depict an "unlocked configuration." In FIG. 11, second rod icon 364, illustrating indicative of an unlocked configuration, is shown on the cylindrical, rounded portion of control rod 300 opposite to second major flat 354. A similar second rod icon 364 (not seen in FIG. 11) is provided on the cylindrical portion of rod 300 opposite to first major flat 344. As best seen in FIG. 11, icons 364 depicting an "unlocked configuration" show a lock in an opened position. Apertures 372, 374, best seen in FIGS. 4 and 6, are formed in end cap 200 to communicate with the cylindrical bored opening 294 to allow icons 362, 364 on control rod 300 to be seen.

System 10 shall now be further described with respect to the assembly and the operation thereof. End cap 200 and the associated components therein are designed such that end cap 200 is always attached to either first arm assembly 50 or second arm assembly 90. Further, end cap 200 is designed such that release of one arm assembly may not take place unless the other arm assembly is in position to be locked to end cap 200.

Referring now to the assembly of end cap 200, before IV pole 42 is attached to end cap 200, end cap 200 is assembled and attached onto one of arm assemblies 50, 90. The following is a description of the assembly of end cap 200 onto first arm assembly 50. Helical springs 276, 278 are placed into cylindrical bores 234, 254. Locking pins 262, 282 are then inserted into cylindrical bores 234, 254, respectively. Extension 72 on first arm assembly 50 is then inserted into main chamber 232a of upper cavity 232. As illustrated in FIG. 3, surface 76 on shoulder 74 on extension 72 engages the end of locking pin 262 and causes locking pin 262 to be forced into cylindrical bore 234 against biasing spring 276. Locking pin 262 is dimensioned such that when extension 72 of first arm assembly 50 is fully inserted into rectangular chamber 232a of upper cavity 232, groove 78 in the face of extension 72 is aligned with bored cylindrical opening 292 in end cap 200, as illustrated in FIG. 4. At the same time, locking pin 262 is moved to an "operative position" by shoulder 74 of extension 72 wherein semi-cylindrical notch 272 in locking pin 262 is also aligned with cylindrical bored opening 292, as illustrated in FIG. 5.

With extension 72 of first arm assembly 50 held in position in end cap 200, locking pin 282 is forced into its associated cylindrical bore 254 by a tool (not shown) such that notch 272 within second locking pin 282 is also aligned with cylindrical bored opening 292. With first and second locking pins 262, 282 and extension 72 of first arm assembly 50 all aligned with bored cylindrical opening 292, control rod 300 may be inserted into end cap 200. Control rod 300 is locked in place in end cap 200 by retaining rings 322. Control rod 300 is rotated to a position, as illustrated in FIGS. 4 and 5, wherein control rod 300 basically captures extension 72 of first arm assembly 50, and at the same time captures first locking pin 262 in the position as shown in FIGS. 4 and 5. In this position, knob 332 on control rod 300 is in a position such that rod icon 334, indicating an "upper locked configuration," is shown, as illustrated in FIG. 3.

With control rod 300 locked into position, the tool holding lower locking pin 282 in place may be removed. As illustrated in FIG. 7, second minor cut-out section 356 of control rod 300 is in registry with cylindrical bore 254 and locking pin 282. As a result, once the tool holding locking pin 282 is removed, biasing spring 278 will operate to force locking pin 282 in a direction out of cylindrical bore 254. However, as indicated in FIG. 7, shoulder 268 defined by flat 266 on locking pin 282 abuts control rod 300 and maintains locking pin 282 within bore 254, thus preventing locking pin 282 from being removed from end cap 200. The foregoing procedure generally illustrates assembly of end cap 200 onto first arm assembly 50. As will be appreciated, end cap 200 may be first assembled onto second arm assembly 90 in a similar fashion.

Once assembled, end cap 200 is maintained in a locked configuration on first arm assembly 50. In this respect, as illustrated in FIG. 7, flat 266 on locking pin 282 preventing rotation of control rod 300 and thus maintains solid portion of control rod 300 in the position shown in FIGS. 4 and 5. In this position, extension 72 of first arm assembly 50 is locked in place, and movement of first locking pin 262 is prevented, as illustrated in FIGS. 4 and 5.

FIG. 3 is an elevational view showing extension 72 of upper arm assembly 50 locked to end cap 200. As shown in FIG. 3, knob icon 334 on knob 332 indicates that extension 72 is locked in upper cavity 232. At the same time, rod icons 362, 364 showing respectively through apertures 372, 374, indicate that first arm assembly 50 in upper cavity 232 is locked, while second arm assembly 90, if in lower cavity 252, is unlocked.

Figure 10:
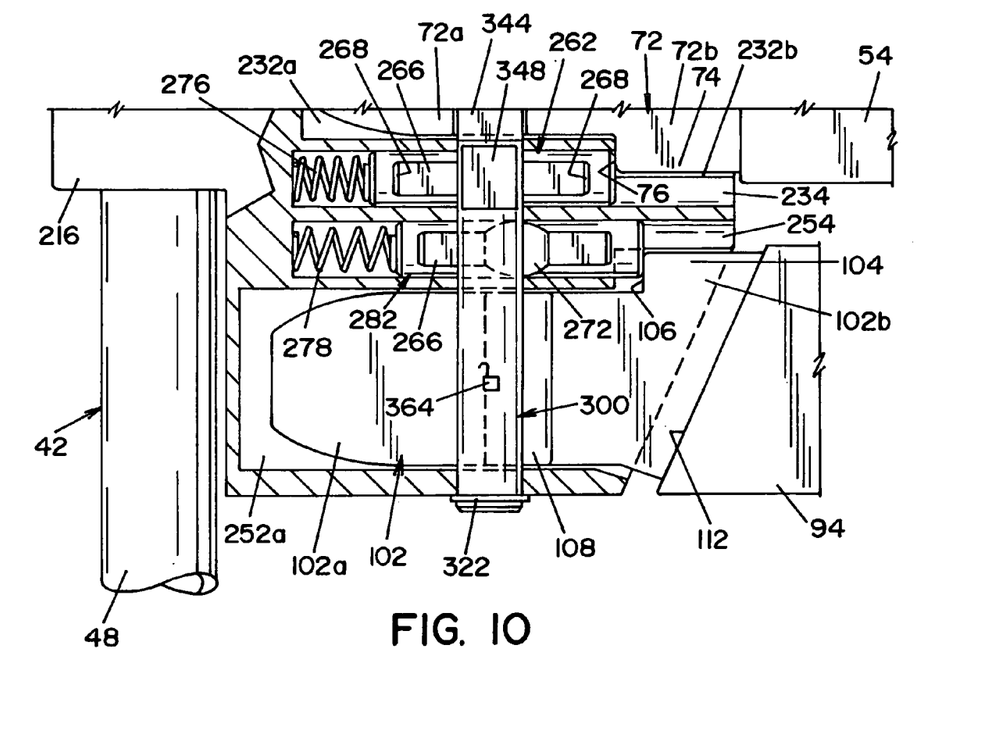
FIG. 10 is a sectional view showing an extension of an arm assembly being inserted into the end cap.

To transfer end cap 200 together with an associated patient care apparatus 12 to second arm assembly 90, extension 102 of second arm assembly 90 is aligned with end cap 200 to be inserted into lower cavity 252. As will be appreciated by those skilled in the art, precise alignment between an arm assembly 50, 90 and cavities 232, 252 in end cap 200 is difficult in real-life situations. The tapered free end of tongue-shaped portions 72a, 102a of extensions 72, 102 facilitates docketing and mating of extensions 72, 102 in end cap 200, when extensions 72, 102 are vertically or rotationally misaligned relative to cavities 232, 252. In this respect, the tapered free ends of tongue-shaped portions 72a, 102a forcibly align extensions 72, 102 with end cap 200 when extensions 72, 102 are inserted, respectively, in cavities 232, 252. Adjustment means 132 on post 122 on patient transfer vehicle 16 may be used to adjust the elevation of second arm assembly 90 relative to end cap 200. Once second arm assembly 90 is at the proper elevation relative to end cap 200, extension 102 of second arm assembly 90 is inserted into rectangular main chamber 252a of second lower cavity 252. As shown in FIG. 10, surface 106 of shoulder 104 on extension 102 forces second locking pin 282 into cylindrical bore 254. Once extension 102 is fully inserted into chamber 252a of lower cavity 252, semi-cylindrical groove 108 on the face of extension 102, as well as semi-cylindrical notch 272 on locking pin 282, will be aligned with control rod 300. Once aligned, control rod 300 may be rotated 180°, wherein the solid portion of control rod 300 is positioned within semi-cylindrical groove 108 in extension 102, and likewise is positioned within semi-cylindrical notch 272 within second locking pin 282. In this position, second arm assembly 90 is then locked to end cap 200. As second arm assembly 90 becomes locked to end cap 200, first arm assembly 50 is released from end cap 200 as a result of solid portion of control rod 300 being rotated out of groove 78 of arm extension 72. As a result, first arm assembly 50 is free to slide out of end cap 200. Control rod 300 is basically a locking member moveable between a first position locking first arm assembly 50 to end cap 200, and a second position locking second arm assembly 90 to end cap 200.

The present invention thus provides a support and transport system 10 for transferring patient care apparatus 12 from one arm assembly to another. In this respect, patient care apparatus 12 may be transferred from a stationary support 14 to a patient transfer vehicle 16, and vice-a-versa, or from one patient transfer vehicle 16 to another patient transfer vehicle 16. System 10 described above provides positive locking of patient care apparatus 12 onto one arm assembly prior to allowing transfer to another arm assembly, thereby reducing the possibility of any damage to hospital apparatus 12 or interruption to the care of a patient.

Figure 12:
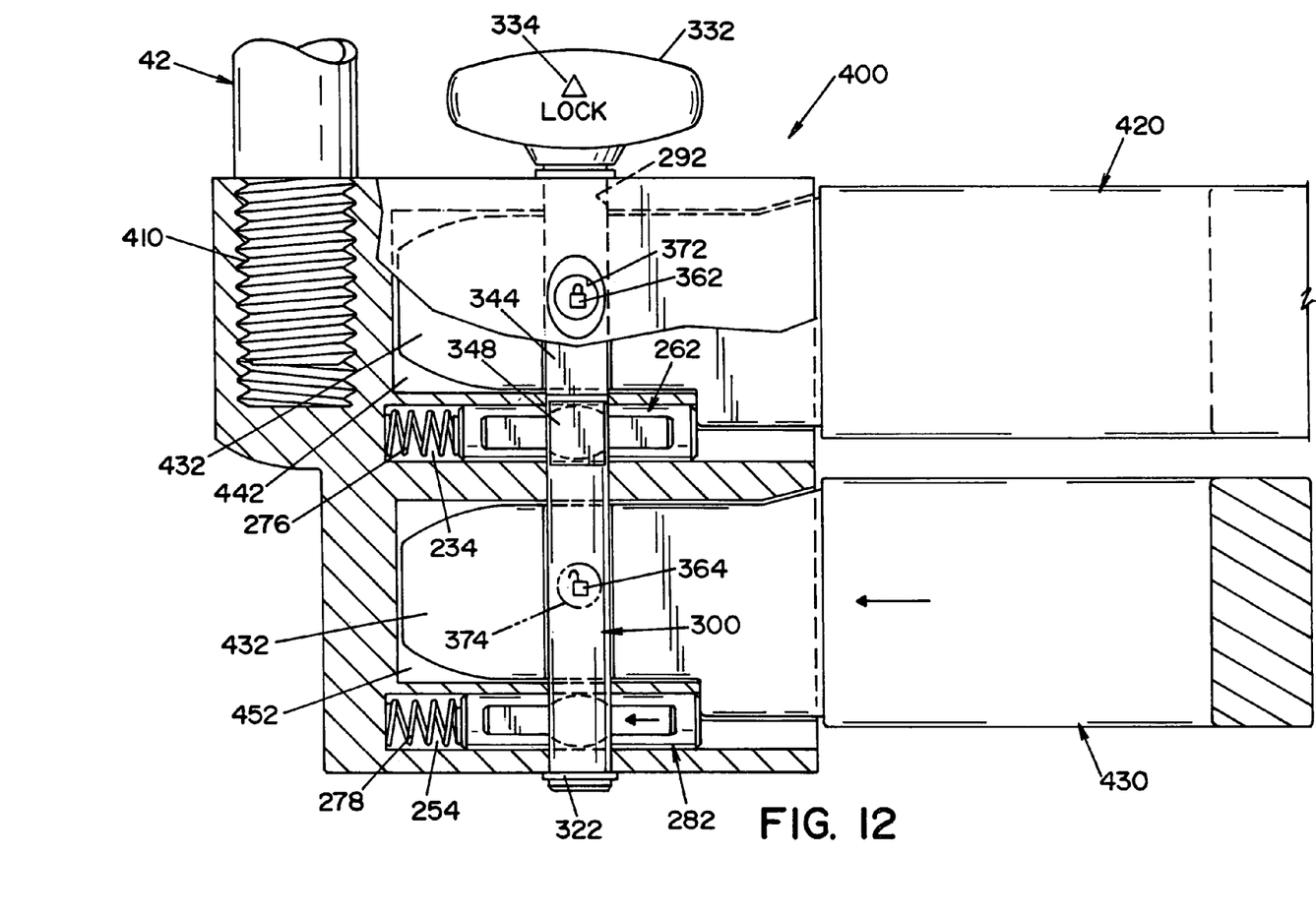
FIG. 12 is a sectional view of an end cap and arm assemblies illustrating alternate embodiments of the present invention.
Figure 13:
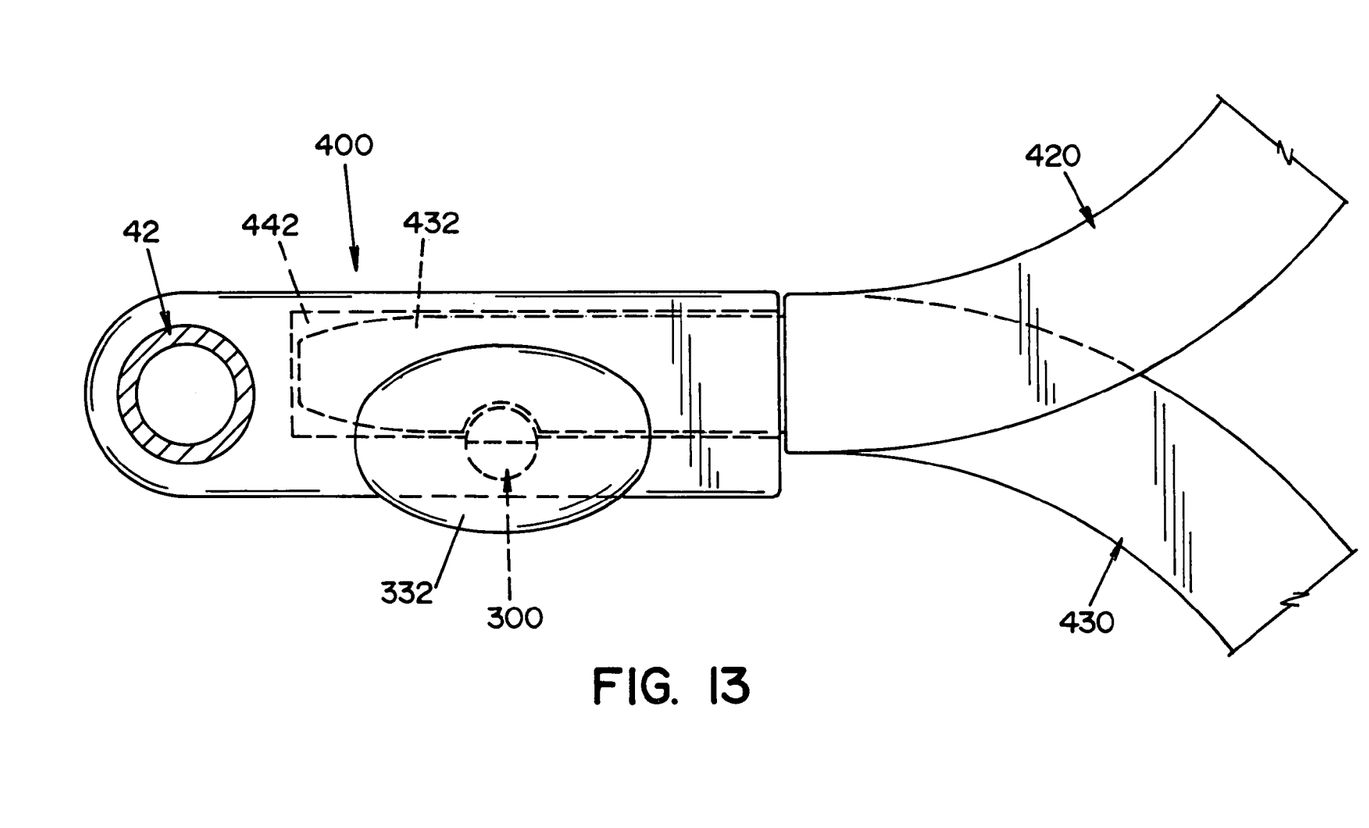
FIG. 13 is a top, plan view of the end cap shown in FIG. 12.

FIGS. 12 and 13 illustrate other embodiments of the present invention. FIGS. 12 and 13 show an end cap 400, wherein patient care apparatus 12, namely an IV pole 42, may be attached to end cap 400 by means of a threaded attachment 410. Similarly, FIG. 12 illustrates an end cap 400 modified such that two arm assemblies 420, 430 may have like extension 432 and wherein either arm assembly 420, 430 may be inserted into upper or lower cavities 442, 452 of end cap 400. Similarly, FIG. 13 illustrates how ends of arm assembly 420, 430 may be curved to eliminate the need to offset one of arm assemblies 420, 430 to facilitate insertion of an arm assembly 420, 430 into end cap 400.

The foregoing description is specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A support and transport system for a patient care apparatus, comprised of:
    a first arm assembly connected to a stationary support, said first arm assembly including an arm having a free end that is movable relative to said stationary support;
    a second arm assembly connected to a patient transfer vehicle, said second arm assembly having a free end;
    an end cap for supporting a patient care apparatus, said end cap being selectively attachable to said free end of first arm assembly and to said free end of said second arm assembly; and
    locking means on said end cap for locking said end cap onto said free end of one of said first and second arm assemblies, the free end of the other of said first and second arm assemblies being detachable from said end cap only when said end cap is locked onto said free end of said one of said first and second arm assemblies.

2. A support and transport system for a patient care apparatus, comprised of:
    a first arm assembly connected to a stationary support, said first arm assembly having a free end;
    a second arm assembly connected to a patient transfer vehicle, said second arm assembly having a free end;
    an end cap for supporting a patient care apparatus, said end cap being selectively attachable to said free end of said first arm assembly and to said free end of said second arm assembly; and
    locking means on said end cap for locking said end cap onto said free end of one of said first and second arm assemblies, the free end of said other of said first and second arm assemblies being detachable from said end cap only when said end cap is locked onto said free end of said one of said first and second arm assemblies, wherein said first arm assembly includes an arm mounted to said stationary support for pivotal movement relative thereto.

3. A support and transport system as defined in claim 2, wherein said first arm assembly includes two arms pivotally connected to each other, one of said two arms being mounted to said stationary support and the other of said two arms having a free end that is attachable to said end cap.

4. A support and transport system as defined in claim 3, wherein said arms are moveable in a horizontal plane.

5. A support and transport system as defined in claim 3, wherein said stationary support is a wall.

6. A support and transport system for a patient care apparatus, comprised of:
    a first arm assembly connected to a stationary support;
    a second arm assembly connected to a patient transfer vehicle;
    an end cap for supporting a patient care apparatus, said end cap being selectively attachable to said first arm assembly and to said second arm assembly; and
    locking means on said end cap for locking said end cap onto one of said first and second arm assemblies, the other of said first and second arm assemblies being detachable from said end cap only when said end cap is locked onto said one of said first and second arm assemblies, wherein said second arm assembly includes an arm mounted to said patient transfer vehicle for pivotal movement relative thereto.

7. A support and transport system as defined in claim 6, wherein said second arm assembly includes two arms pivotally connected to each other, one of said two arms being mounted to said patient transfer vehicle and the other of said two arms having a free end that is attachable to said end cap.

8. A support and transport system as defined in claim 7, wherein said arms are moveable in a horizontal plane.

9. A support and transport system as defined in claim 6, further comprising:
    means for vertically adjusting the position of said second arm assembly relative to said patient transfer vehicle.

10. A support and transport system as defined in claim 6, wherein said patient transfer vehicle is a hospital bed.

11. A support and transport system as defined in claim 1, wherein said end cap includes attachment means for releasably attaching a patient care apparatus to said end cap.

12. A support and transport system as defined in claim 11, wherein said attachment means is a collar clamp.

13. A support and transport system as defined in claim 11, wherein said patient care apparatus is an IV pole.

14. A support and transport system for a patient care apparatus, comprised of:
    a first arm assembly connected to a stationary support;
    a second arm assembly connected to a patient transfer vehicle;
    an end cap for supporting a patient care apparatus, said end cap being selectively attachable to said first arm assembly and to said second arm assembly; and
    locking means on said end cap for locking said end cap onto one of said first and second arm assemblies, the other of said first and second arm assemblies being detachable from said end cap only when said end cap is locked onto said one of said first and second arm assemblies, wherein said end cap includes two cavities dimensioned to receive the free ends of said first and second arm assemblies, and wherein said end cap includes attachment means for releasably attaching a patient care apparatus to said end cap.

15. A support and transport system as defined in claim 14, wherein said locking means includes:
    a control member moveable between a first position locking said first arm assembly to said end cap and a second position locking said second arm assembly to said end cap, and
    a locking pin associated with each of said cavities, said locking pins permitting movement of said control member between said first and second positions when each of said locking pins is disposed in a predetermined position relative to said control member.

16. A support and transport system as defined in claim 15, wherein said locking pins are in said predetermined positions when the ends of said first and second arm assemblies are positioned within the cavities of said end cap.

17. A support and transport system as defined in claim 16, wherein the free ends of said first and second arm assemblies operatively engage said locking pins when said free ends are inserted within the cavities to move said locking pins to said predetermined position.

18. A support and transport system as defined in claim 15, wherein said first arm assembly is locked to end cap when said second arm assembly is unlocked and removable from said end cap, and vice-a-versa.

19. A support and transport system as defined in claim 15, wherein each locking pin is biased away from said predetermined position when an associated arm assembly is removed from said end cap.

20. A support and transport system as defined in claim 19, wherein said locking pins are in said predetermined positions when the ends of said first and second arm assemblies are positioned within the cavities of said end cap.

21. A support and transport system as defined in claim 20, wherein the free ends of said first and second arm assemblies operatively engage said locking pins when said free ends are inserted within the cavities to move said locking pins to said predetermined position.

22. In combination:
an IV pole;
a first arm assembly connectable to a stationary support, said first arm assembly including an arm having a free end that is movable relative to said stationary support;
a second arm assembly connectable to a patient transfer vehicle, said second arm assembly having a free end;
an end cap for supporting said IV pole, said end cap being selectively attachable to said free end of said first arm assembly and to said free end of said second arm assembly; and
locking means on said end cap for locking said end cap onto the free end of one of said first and second arm assemblies, the free end of the other of said first and second arm assemblies being detachable from said end cap only when said end cap is locked onto the free end of said one of said first and second arm assemblies.

23. In combination:
an IV pole;
a first arm assembly connectable to a stationary support, said first arm assembly having a free end;
a second arm assembly connectable to a patient transfer vehicle, said second arm assembly having a free end;
an end cap for supporting said IV pole, said end cap being selectively attachable to said free end of said first arm assembly and to said free end of said second arm assembly; and
locking means on said end cap for locking said end cap onto the free end of one of said first and second arm assemblies, the free end of the other of said first and second arm assemblies being detachable from said end cap only when said end cap is locked onto said free end of said one of said first and second arm assemblies, wherein said first arm assembly includes an arm mounted to said stationary support for pivotal movement relative thereto.

24. A support and transport system as defined in claim 23, wherein said first arm assembly includes two arms pivotally connected to each other, one of said two arms being mounted to said stationary support and the other of said two arms having a free end that is attachable to said end cap.

25. A support and transport system as defined in claim 24, wherein said arms are moveable in a horizontal plane.

26. A support and transport system as defined in claim 24, wherein said stationary support is a wall.

27. In combination:
an IV pole;
a first arm assembly connectable to a stationary support;
a second arm assembly connectable to a patient transfer vehicle;
an end cap for supporting said IV pole, said end cap being selectively attachable to said first arm assembly and to said second arm assembly; and
locking means on said end cap for locking said end cap onto one of said first and second arm assemblies, the other of said first and second arm assemblies being detachable from said end cap only when said end cap is Locked onto said one of said first and second arm assemblies, wherein said second arm assembly includes an arm mounted to said patient transfer vehicle for pivotal movement relative thereto.

28. A support and transport system as defined in claim 27, wherein said second arm assembly includes two arms pivotally connected to each other, one of said two arms being mounted to said patient transfer vehicle and the other of said two arms having a free end that is attachable to said end cap.

29. A support and transport system as defined in claim 28, wherein said arms are moveable in a horizontal plane.

30. A support and transport system as defined in claim 27, further comprising:
means for vertically adjusting the position of said second arm assembly relative to said patient transfer vehicle.

31. A support and transport system as defined in claim 27, wherein said patient transfer vehicle is a hospital bed.

32. In combination:
an IV pole;
a first arm assembly connectable to a stationary support, said first arm assembly having a free end;
a second arm assembly connectable to a patient transfer vehicle, said second arm assembly having a free end;
an end cap for supporting said IV pole, said end cap being selectively attachable to the free end of said first arm assembly and to the free end of said second arm assembly; and
locking means on said end cap for locking said end cap onto the free end of one of said first and second arm assemblies, the free end of the other of said first and second arm assemblies being detachable from said end cap only when said end cap is locked onto said free end of said one of said first and second arm assemblies, wherein said end cap includes attachment means for releasably attaching an IV pole to said end cap.

33. A support and transport system as defined in claim 32, wherein said attachment means is a collar clamp.

34. A support and transport system as defined in claim 32, wherein said IV pole is threaded into said end cap.

35. A support and transport system as defined in claim 32, wherein said end cap includes two cavities dimensioned to receive the free ends of said first and second arm assemblies.

36. A support and transport system as defined in claim 35, wherein said locking means includes:
a control member moveable between a first position locking said first arm assembly to said end cap and a second position locking said second arm assembly to said end cap, and
a locking pin associated with each of said cavities, said locking pins permitting movement of said control member between said first and second positions when each of said locking pins is disposed in a predetermined position relative to said control member.

37. A support and transport system as defined in chum 36, wherein said locking pins are in said predetermined positions when the ends of said first and second arm assemblies are positioned within the cavities of said end cap.

38. A support and transport system as defined in claim 37, wherein the free ends of said first and second arm assemblies operatively engage said locking pins when said free ends are inserted within the cavities to move said locking pins to said predetermined position.

39. A support and transport system as defined in claim 36, wherein said first arm assembly is locked to the end cap when said second arm assembly is unlocked and removable from said end cap, and vice-a-versa.

40. A support and transport system as defined in claim 36, wherein each locking pin is biased away from said predetermined position when an associated arm assembly is removed from said end cap.

41. A support and transport system as defined in claim 40, wherein said locking pins are in said predetermined positions when the ends of said first and second arm assemblies are positioned within the cavities of said end cap.

42. A support and transport system as defined in claim 41, wherein the free ends of said first and second arm assemblies operatively engage said locking pins when said free ends are inserted within the cavities to move said locking pins to said predetermined position.

43. A support and transport system for a patient care apparatus, comprised of:
    a first arm assembly connected to a first structure, said first arm assembly including an arm having a free end that is movable relative to said first structure;
    a second arm assembly connected to a second structure said second arm assembly including a free end;
    an end cap for supporting a patient care apparatus, said end cap being selectively attachable to said free end of said first arm assembly and to said free end of said second arm assembly; and
    locking means on said end cap for locking said end cap onto said free end of one of said first and second arm assemblies, the free end of the other of said first and second arm assemblies being detachable from said end cap only when said end cap is locked onto said free end of said one of said first and second arm assemblies.

44. A support and transport system for a patient care apparatus, comprised of
    a first arm assembly connected to a first structure, said first arm assembly having a free end;
    a second arm assembly connected to a second structure said second arm assembly having a free end;
    an end cap for supporting a patient care apparatus, said end cap being selectively attachable to said free end of first arm assembly and to said free end of said second arm assembly; and
    locking means on said end cap for locking said end cap onto said free end of one of said first and second arm assemblies, the free end of the other of said first and second arm assemblies being detachable from said end cap only when said end cap is locked onto said free end of said one of said first and second arm assemblies, wherein said first arm assembly includes an arm mounted to said first structure for pivotal movement relative thereto.

45. A support and transport system as defined in claim 44, wherein said first arm assembly includes two arms pivotally connected to each other, one of said two arms being mounted to said first structure and the other of said two arms having a free end that is attachable to said end cap.

46. A support and transport system as defined in claim 45, wherein said first structure is a stationary support.

47. A support and transport system as defined in claim 46, wherein said stationary support is a wall.

48. A support and transport system as defined in claim 45, wherein said first structure is a patient transfer vehicle.

49. A support and transport system for a patient care apparatus, comprised of:
    a first arm assembly connected to a first structure;
    a second arm assembly connected to a second structure;
    an end cap for supporting a patient care apparatus, said end cap being selectively attachable to said first arm assembly and to said second arm assembly; and
    locking means on said end cap for locking said end cap onto one of said first and second arm assemblies, the other of said first and second arm assemblies being detachable from said end cap only when said end cap is locked onto said one of said first and second arm assemblies, wherein said second arm assembly includes an arm mounted to said second structure for pivotal movement relative thereto.

50. A support and transport system as defined in claim 49, wherein said second arm assembly includes two arms pivotally connected to each other, one of said two arms being mounted to said second structure and the other of said two arms having a free end that is attachable to said end cap.

51. A support and transport system as defined in claim 50, wherein said second structure is a stationary support.

52. A support and transport system as defined in claim 50, wherein said second structure is a patient transfer vehicle.

53. A support and transport system for a patient care apparatus, comprised of:
    a first arm assembly connected to a first structure, said first arm assembly having a free end;
    a second arm assembly connected to a second structure, said second arm assembly having a free end;
    an end cap for supporting a patient care apparatus, said end cap being selectively attachable to said free end of first arm assembly and to said free end of said second arm assembly; and
    locking means on said end cap for locking said end cap onto said free end of one of said first and second arm assemblies, the free end of the other of said first and second arm assemblies being detachable from said end cap only when said end cap is locked onto said free end of said one of said first and second arm assemblies, wherein said end cap includes attachment means for releasably attaching a patient care apparatus to said end cap.

54. A support and transport system as defined in claim 53, wherein said attachment means is a collar clamp.

55. A support and transport system for a patient care apparatus, comprised of:
    a first arm assembly connected to a first structure, said first arm assembly having a free end;
    a second arm assembly connected to a second structure, said second arm assembly having a free end;
    an end cap for supporting a patient care apparatus, said end cap being selectively attachable to said free end of first arm assembly and to said free end of said second arm assembly; and
    locking means on said end cap for locking said end cap onto said free end of one of said first and second arm assemblies, the free end of the other of said first and second arm assemblies being detachable from said end cap only when said end cap is locked onto said free end of said one of said first and second arm assemblies, wherein said patient care apparatus is an IV pole.

56. A support and transport system as defined in claim 55, wherein said IV pole is threaded into said end cap.

57. A support and transport system as defined in claim 53, wherein said end cap includes two cavities dimensioned to receive the free ends of said first and second arm assemblies.

58. A support and transport system as defined in claim 57, wherein said locking means includes:
- a control member moveable between a first position locking said first arm assembly to said end cap and a second position locking said second arm assembly to said end cap, and
- a locking pin associated with each of said cavities, said locking pins permitting movement of said control member between said first and second positions when each of said locking pins is disposed in a predetermined position relative to said control member.

59. A support and transport system as defined in claim 58, wherein said locking pins are in said predetermined positions when the ends of said first and second arm assemblies are positioned within the cavities of said end cap.

60. A support and transport system as defined in claim 59, wherein the free ends of said first and second arm assemblies operatively engage said locking pins when said free ends are inserted within the cavities to move said locking pins to said predetermined position.

61. A support and transport system as defined in claim 58, wherein said first arm assembly is locked to end cap when said second arm assembly is unlocked and removable from said end cap, and vice-a-versa.

62. A support and transport system as defined in claim 58, wherein each locking pin is biased away from said predetermined position when an associated arm assembly is removed from said end cap.

63. A support and transport system as defined in claim 62, wherein said locking pins are in said predetermined positions when the ends of said first and second arm assemblies are positioned within the cavities of said end cap.

64. A support and transport system as defined in claim 63, wherein the free ends of said first and second arm assemblies operatively engage said locking pins when said free ends are inserted within the cavities to move said locking pins to said predetermined position.

\* \* \* \* \*